US009750626B2

(12) United States Patent
Hadley (10) Patent No.: US 9,750,626 B2
(45) Date of Patent: Sep. 5, 2017

(54) APPARATUS AND METHODS FOR IMPROVED STENT DEPLOYMENT

(71) Applicant: Cook Medical Technologies LLC, Bloomington, IN (US)

(72) Inventor: Rick Hadley, Otterbein, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 273 days.

(21) Appl. No.: 14/062,142

(22) Filed: Oct. 24, 2013

(65) Prior Publication Data

US 2014/0121754 A1 May 1, 2014

Related U.S. Application Data

(60) Provisional application No. 61/720,802, filed on Oct. 31, 2012.

(51) Int. Cl.
*A61F 2/966* (2013.01)
*A61F 2/95* (2013.01)
(Continued)

(52) U.S. Cl.
CPC .................. *A61F 2/95* (2013.01); *A61F 2/07* (2013.01); *A61F 2/966* (2013.01);
(Continued)

(58) Field of Classification Search
CPC .. A61F 2/962; A61F 2/966; A61F 2002/9511; A61F 2002/9655
(Continued)

(56) References Cited

U.S. PATENT DOCUMENTS 5,480,423 A   1/1996  Ravenscroft et al.
5,683,451 A  11/1997  Lenker et al.
(Continued)

FOREIGN PATENT DOCUMENTS

DE  10 2006 053748 B3   4/2008
WO       WO96/09013      3/1996
(Continued)

OTHER PUBLICATIONS

Search Report for European Patent Application No. 13191137.2 dated Jan. 29, 2014, 7 pgs.
(Continued)

*Primary Examiner* — Kathleen Holwerda
(74) *Attorney, Agent, or Firm* — Brinks Gilson & Lione (57) ABSTRACT

The present embodiments provide systems and methods for facilitating deployment of a stent. In one embodiment, the system comprises an inner cannula, and at least one trigger wire extends at least partially within a lumen of the inner cannula and has an exposed portion extending radially outside of the lumen of the inner cannula. The exposed portion of the at least one trigger wire engages an associated portion of a stent in a delivery state. An outer cannula is sized for longitudinal movement over a portion of the inner cannula. Selective distal retraction of the outer cannula permits partial deployment of the stent to an extent of slack provided by the at least one trigger wire, and selective proximal advancement of the outer cannula incrementally urges the exposed portion of the at least one trigger wire radially inward to constrain the associated portion of the stent.

20 Claims, 7 Drawing Sheets

(51) Int. Cl.
*A61F 2/07* (2013.01)
*A61F 2/848* (2013.01)

(52) U.S. Cl.
CPC .............. *A61F 2002/8483* (2013.01); *A61F 2002/9511* (2013.01); *A61F 2002/9665* (2013.01)

(58) Field of Classification Search
USPC ................................ 623/1.11, 1.12
See application file for complete search history.

(56) References Cited

U.S. PATENT DOCUMENTS

| | | | |
|---|---|---|---|
| 5,902,263 A | 5/1999 | Patterson et al. | |
| 5,948,017 A | 9/1999 | Taheri | |
| 6,656,212 B2 | 12/2003 | Ravenscroft et al. | |
| 6,764,503 B1 | 7/2004 | Ishimaru | |
| 6,872,224 B1* | 3/2005 | Telxelra Moretra | A61M 25/00 606/108 |
| 2001/0001833 A1 | 5/2001 | Ravenscroft et al. | |
| 2001/0034548 A1* | 10/2001 | Vrba | A61F 2/01 623/1.11 |
| 2002/0120277 A1 | 8/2002 | Hauschild et al. | |
| 2002/0151954 A1 | 10/2002 | Brenneman | |
| 2003/0135269 A1 | 7/2003 | Swanstrom | |
| 2003/0233140 A1* | 12/2003 | Hartley | A61F 2/95 623/1.11 |
| 2004/0220653 A1 | 11/2004 | Borg et al. | |
| 2004/0220655 A1 | 11/2004 | Swanson et al. | |
| 2005/0197694 A1 | 9/2005 | Pai et al. | |
| 2005/0288764 A1* | 12/2005 | Snow | A61F 2/95 623/1.11 |
| 2006/0020319 A1 | 1/2006 | Kim et al. | |
| 2006/0069422 A9 | 3/2006 | Bolduc et al. | |
| 2006/0095116 A1 | 5/2006 | Bolduc et al. | |
| 2007/0088431 A1 | 4/2007 | Bourang et al. | |
| 2007/0135826 A1 | 6/2007 | Zaver et al. | |
| 2008/0027529 A1* | 1/2008 | Hartley | A61F 2/07 623/1.11 |
| 2008/0140178 A1* | 6/2008 | Rasmussen | A61F 2/95 623/1.11 |
| 2009/0030497 A1* | 1/2009 | Metcalf | A61F 2/95 623/1.12 |
| 2009/0204202 A1* | 8/2009 | Dierking | A61F 2/91 623/1.16 |
| 2011/0288624 A1* | 11/2011 | Roeder | A61F 2/07 623/1.11 |

FOREIGN PATENT DOCUMENTS

| | | |
|---|---|---|
| WO | WO2006/005082 | 1/2006 |
| WO | WO2007/022496 | 2/2007 |
| WO | WO2010/027485 | 3/2010 |

OTHER PUBLICATIONS

Response to Search Report for European Patent Application No. 13191137.2 dated May 20, 2014, 21 pgs.
International Search Report and Written Opinion for PCT/US2009/004994 dated Dec. 10, 2009, 17 pgs.
Intention to Grant for EP13191137.2 dated Nov. 15, 2016, 34 pgs.

* cited by examiner

APPARATUS AND METHODS FOR IMPROVED STENT DEPLOYMENT

PRIORITY CLAIM

This invention claims the benefit of priority of U.S. Provisional Application Ser. No. 61/720,802, entitled "Apparatus and Methods for Improved Stent Deployment," filed Oct. 31, 2012, the disclosure of which is hereby incorporated by reference in its entirety.

BACKGROUND

The present invention relates generally to medical devices, and more particularly, to apparatus and methods for improved deployment of stents.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter. Trigger wires also may be used in conjunction with different stent designs, such as cannula-cut stents having acute or pointed bends. In the latter embodiment, the trigger wires may be looped around one or more vertices formed beneath the proximal and/or distal apices, e.g., a location where an individual apex splits into two separate strut segments.

If trigger wires are used to deploy stents, typically the actuation of the trigger wire causes full radial expansion of the stent, such that the stent engages an inner wall of a duct, vessel or the like. Barbs of the stent may engage the body passage, and the deployed stent may be difficult or impossible to recapture or reposition at this time. Further, upon release of the trigger wire, as the stent is expanding it may foreshorten or otherwise move an undesired amount with respect to the body passage. Therefore, the actuation of a conventional trigger wire may yield inaccurate positioning of a stent that engages a body passage and may be difficult to retrieve.

SUMMARY

The present embodiments provide systems and methods for facilitating deployment of a stent. In one embodiment, the system comprises an inner cannula having proximal and distal ends. At least one trigger wire extends at least partially within a lumen of the inner cannula and has an exposed portion extending radially outside of the lumen of the inner cannula. The exposed portion of the at least one trigger wire engages an associated portion of a stent in a delivery state. An outer cannula is sized for longitudinal movement over a portion of the inner cannula.

Selective distal retraction of the outer cannula distally beyond the exposed portion of the trigger wire permits partial deployment of the stent to an extent of slack provided by the at least one trigger wire. Further, selective proximal advancement of the outer cannula over the exposed portion of the at least one trigger wire incrementally urges the exposed portion of the at least one trigger wire in a radially inward direction to radially constrain the associated portion of the stent.

Advantageously, the provision of a delivery system employing the apparatus and methods described herein may permit improved positioning of a stent, or stent-graft, inside of a body passage. The apparatus and methods also permit an amount of recapture of a stent prior to full deployment. Moreover, any undesirable foreshortening may be reduced or eliminated.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
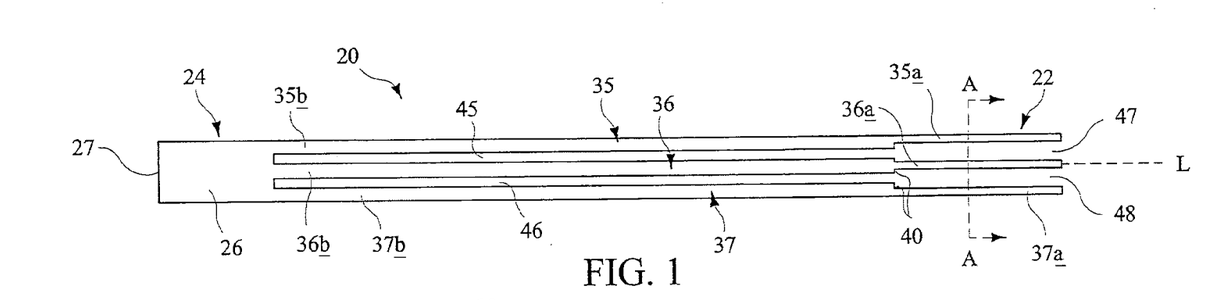
FIG. 1 is a side view of an exemplary control member in a contracted state.
Figures 2, 3:
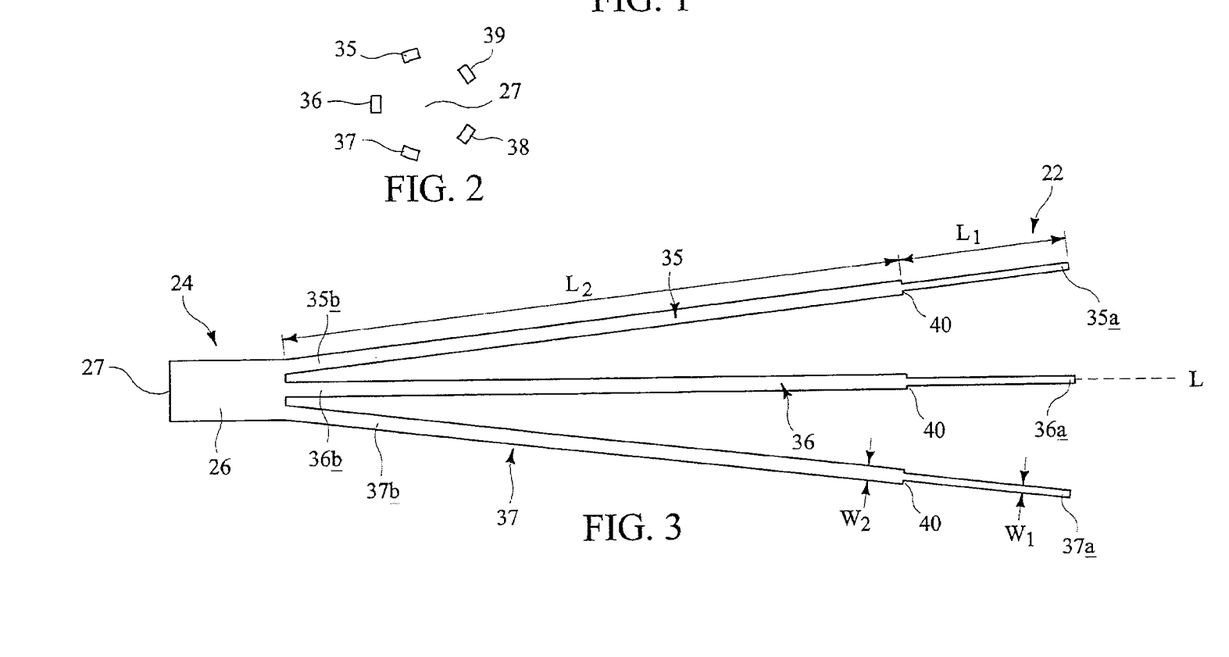
FIG. 2 is a cross-sectional view along line A-A of FIG. 1.
FIG. 3 is a side view of the control member of FIG. 1 in a partially or fully expanded state.

Referring to FIGS. 1-3, an apparatus for deploying a stent, or stent-graft, is disclosed. The apparatus comprises a control member 20 having proximal and distal regions 22 and 24. The control member 20 may be formed from a cannula 26 having a lumen 27 extending between the proximal and distal regions 22 and 24. As described further below, selective actuation of the control member 20 may permit at least partial radial expansion of a stent within a body passage, and also may permit at least partial radial contraction of the stent to permit repositioning of the stent within the body passage.

The cannula 26 of the control member 20 may comprise a shape-memory material such as a nickel-titanium alloy, or alternatively, stainless steel or another suitable material, as explained below. The proximal region 22 of the control member 20 comprises at least one tine member configured to engage a portion of a stent. The control member 20 may include a plurality of tine members. For example, as shown in FIGS. 1-3, the control member 20 comprises five tine members 35-39 disposed about the circumference of the control member 20, as best seen in FIG. 2, although only three tine members 35-37 are shown for clarity in the side views of FIG. 1 and FIG. 3. Any number of tine members may be employed, i.e., greater or fewer than five tine members.

The tine member 35-39 each comprise proximal and distal regions. As shown in FIG. 1, the tine member 35 comprises a proximal region 35a and a distal region 35b, while the tine member 36 comprises a proximal region 36a and a distal region 36b, and the tine member 37 comprises a proximal region 37a and a distal region 37b. The proximal regions of the tine members may form a tip that may be tapered or blunt.

The tine members 35-39 may be formed into the cannula 26 by forming one or more longitudinal slits in lateral surfaces of the cannula 26, e.g., using a laser or other suitable cutting technique, along the proximal region 22 of the control member 20. The tine members also may be attached to the cannula 26 by soldering, welding, or other methods. The provision of a proximal longitudinal slit 47 separates the proximal regions 35a and 36a of the adjacent tine members 35 and 36. Similarly, a proximal longitudinal slit 48 separates the proximal regions 36a and 37a of the adjacent tine members 36 and 37. Further, the provision of a distal longitudinal slit 45 formed into the cannula 26 separates the distal regions 35b and 36b of adjacent tine members 35 and 36, respectively, while the provision of a distal longitudinal slit 46 formed into the cannula 26 separates the distal regions 36b and 37b of adjacent tine members 36 and 37, respectively, as shown FIG. 1.

In one embodiment, a length of the proximal longitudinal slits 47 and 48 is less than a length of the distal longitudinal slits 45 and 46. Accordingly, the proximal regions of the tine members 35-39 comprise a length $L_1$, while the distal regions of the tine members 35-39 comprise a length $L_2$, whereby the length $L_1$ is less than the length $L_2$, as shown in FIG. 3. In one example, the length $L_2$ is about 2 to 8 times greater than the length $L_1$. Solely by way of example, the length $L_2$ may range from about 2 to 20 cm, while the length $L_1$ may range from about 0.5 to about 6 cm. The length $L_1$ preferably is sufficient to cause the proximal regions of one or more tine members 35-39 to engage a portion of a stent, e.g., by being disposed through a bore of the stent, as described in FIGS. 9-10 below.

Further, the proximal longitudinal slits 47 and 48 preferably are circumferentially wider than the distal longitudinal slits 45 and 46. Accordingly the proximal regions of the tine members 35-39 comprise a width $w_1$, while the distal regions of the tine members 35-39 comprise a width $w_2$, whereby the width $w_1$ is less than the width $w_2$, as shown in FIG. 3. Therefore, a stepped portion 40 is formed where the proximal regions 35a-37a transition into the wider distal regions 35b-37b, as shown in FIG. 1 and FIG. 3. The stepped portion 40 preferably is sized and configured to engage and/or abut a portion of a stent, for purposes explained further below.

The control member 20 comprises a contracted delivery configuration, shown in FIG. 1, and further comprises a partially or fully deployed expanded configuration, as shown in FIG. 3. In the contracted delivery configuration, the proximal regions of the tine members 35-39 are radially contracted, such that they preferably are substantially parallel to a central longitudinal axis L of the control member 20, as generally depicted in FIG. 1. In the partially or fully expanded configurations, the proximal region of at least one of the tine members 35-39 expands radially outward relative to the central longitudinal axis L, as depicted in FIG. 3.

As explained with regard to FIGS. 9-10 below, the tine members 35-39 are selectively movable in incremental amounts between the contracted and expanded configurations shown in FIGS. 1 and 3, respectively. In one exemplary method, described below, the proximal regions of the tine members 35-39 are selectively movable in incremental amounts in both radially inward and outward directions, to facilitate positioning of a stent within a body passage in a controlled manner.

Figure 4:
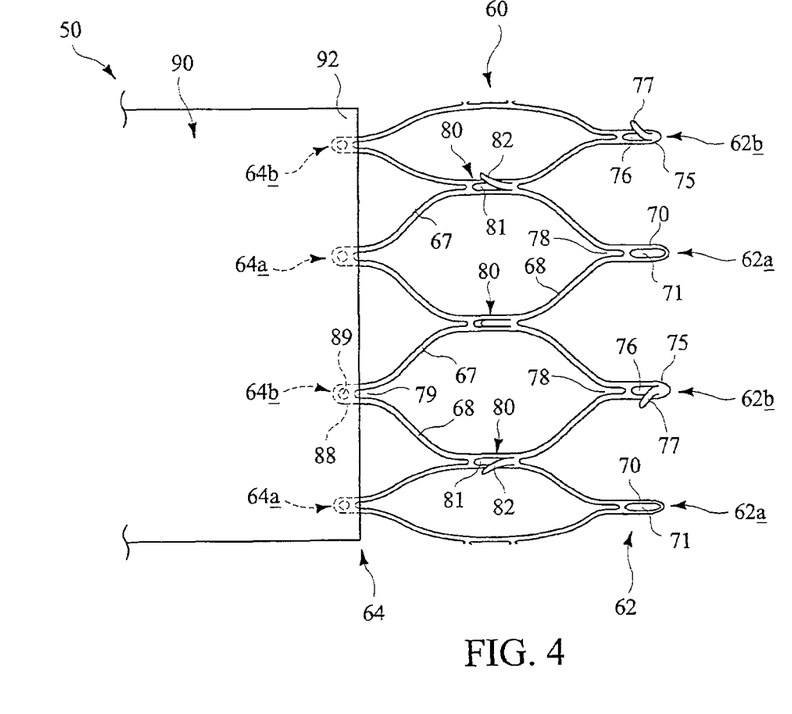
FIG. 4 is a side view depicting a proximal region of an exemplary stent-graft for used with the control member of FIGS. 1-3.

Referring now to FIG. 4, an exemplary stent-graft 50, having a proximally-located stent 60 coupled to a graft material 90, may be deployed in a controlled manner using the control member 20 of FIGS. 1-3. The stent 60 may be manufactured from a continuous cylinder into which a pattern may be cut by a laser or by chemical etching to produce slits in the wall of the cylinder. The resulting structure may then be heat set to give it a desired final configuration. As shown in FIG. 4, the final configuration may include a shape having a series of proximal apices and a series of distal apices. A proximal end 62 of the stent 60 may comprise multiple adjacent proximal apices 62a and 62b, while a distal end 64 of the stent 20 may comprise multiple adjacent distal apices 64a and 64b, as shown in FIG. 4. The stent 60 may be provided in accordance with a self-expanding attachment stent, for example, described in U.S. Patent Publication 2009/0204202, which is hereby incorporated by reference in its entirety.

In FIG. 4, at least one pair of adjacent, proximal apices 62a and 62b may comprise different features. For example, as shown in FIG. 4, a first proximal apex 62a may comprise an end region 70 having a bore 71 formed therein, wherein the bore 71 is configured to receive a proximal region of one of the tine members 35-39, as explained further below. A second, adjacent proximal apex 62b may comprise an end region 75 having an integral barb 77 formed therein, as shown in FIG. 4. The barb 77 may be formed by laser cutting a desired barb shape into the end regions 75. A slit 76 therefore is formed into each end region 75 after the desired barb shape is formed, as shown in FIG. 4. Once the desired barb shape is cut, a main body of the barb 77 may be bent in a radially outward direction with respect to the end region 75. The angle may comprise any acute angle, or alternatively may be substantially orthogonal or obtuse. If desired, the barb 77 may be sharpened, for example, by grinding the tip of the barb, to facilitate engagement at a target tissue site.

Referring still to FIG. 4, the stent 60 may comprise at least one strut segment disposed between the proximal and distal apices. For example, multiple angled strut segments may be disposed between a first proximal apex 62a and a corresponding distal apex 64a, and an identical set of angled strut segments may be disposed between an adjacent, second proximal apex 62b and a corresponding distal apex 64b. By way of example, a first proximal apex 62a extends distally and splits into first and second angled strut segments 67 and 68, respectively, thereby forming a proximal vertex 78, as shown in FIG. 4. In a compressed state, the first and second angled strut segments 67 and 68 may be compressed such that they are substantially parallel to one another. Similarly, each distal apex 64a and 64b may extend in a proximal direction and split into the first and second angled strut segments 67 and 68, respectively, thereby forming a distal vertex 79. A first angled strut segments 67 may meet with an adjacent second angled strut segment 68, thereby forming a transition region 80. In this manner, the stent 60 may be formed into a continuous, generally cylindrical shape, as shown in FIG. 4.

Expansion of the stent 60 is at least partly provided by the angled strut segments 67 and 68, which may be substantially parallel to one another in a compressed state, but may tend to bow outward away from one another in the expanded state shown in FIG. 4. The stent 60 may be formed from any suitable material, such as a laser-cut nitinol cannula. If manufactured from nitinol, the stent 60 may be inclined to assume the expanded state shown in FIG. 4 upon removal of a delivery sheath, such as the outer sheath 140 of FIG. 8 below.

Each transition region 80 may comprise a larger surface area relative to the angled segments, since the transition regions are composed substantially of multiple different angled segments 67 and 68. The stent 60 may comprise at least one barb 82 disposed in at least one of the transition regions 80. The barb 82 may be formed integrally, as part of the strut, or may comprise an external barb that is adhered to a surface of the transition regions 80. As shown in FIG. 4, multiple integral barbs 82 are provided. Like the barbs 77 noted above, the barbs 82 may be formed by laser cutting a desired barb shape into the transition regions 80. A slit 81 therefore is formed into the transition region 80 after the desired barb shape is formed, as shown in FIG. 4. Since the transition regions 80 may comprise an increased surface area relative to other regions of the stent 60, it may be easier to perforate portions of the transition regions 80 without adversely affecting the structural integrity of the stent. Once the desired barb shape is cut, a main body of the barb 82 may be bent in an outward direction at any angle with respect to the transition region 80 and optionally may be sharpened to facilitate engagement at a target tissue site.

Each of the distal apices 62a and 62b may comprise an end region 88 having a bore 89 formed therein, as shown in FIG. 4. The distal end 64 of the stent 80 may be coupled to a proximal end 92 of the graft material 90. The distal apices 62a and 62b may be coupled to the graft material, for example, using one or more sutures that are looped through the graft material and the bores 89 of the stent 80. In this manner, the stent 60 may be used as an attachment stent for endovascular graft fixation. For example, the graft material 90 may overlap with an aneurysm to seal off fluid flow into the aneurysm, while the proximal end 62 of the stent 60 may extend in a proximal direction away from the graft material, e.g., to engage a healthy portion of a vessel wall away from a diseased portion of the aneurysm. As will be apparent, one or more additional stents may be coupled to an inner or outer surface of the graft material 90, i.e., at a location distal to the stent 60, to help maintain patency throughout the graft material.

The stent 60 has a reduced diameter delivery state so that it may be advanced to a target location within a vessel or duct. The stent 60 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 60. Further, the struts of the stent 60 may comprise a substantially flat wire profile or may comprise a rounded profile. As best seen in FIG. 4, the struts of the stent 60 generally comprise a flat wire profile.

The stent 60 may be manufactured from a super-elastic material. Solely by way of example, the super-elastic material may comprise a shape-memory alloy, such as a nickel titanium alloy (nitinol). If the stent 60 comprises a self-expanding material such as nitinol, the stent may be heat-set into the desired expanded state, whereby the stent 60 can assume a relaxed configuration in which it assumes the preconfigured first expanded inner diameter upon application of a certain cold or hot medium. Alternatively, the stent 60 may be made from other metals and alloys that allow the stent 60 to return to its original, expanded configuration upon deployment, without inducing a permanent strain on the material due to compression. Solely by way of example, the stent 60 may comprise other materials such as stainless steel, cobalt-chrome alloys, amorphous metals, tantalum, platinum, gold and titanium. The stent 60 also may be made from non-metallic materials, such as thermoplastics and other polymers.

While one exemplary stent 60 is shown in FIG. 4 and described in FIGS. 9-10 below, various alternative stent configurations may be used in conjunction with the control member 20 of FIGS. 1-3 and the other apparatus described further in FIGS. 5-10 below. Moreover, the stent may be deployed alone, or as part of a stent-graft system, as depicted herein.

Figure 5:
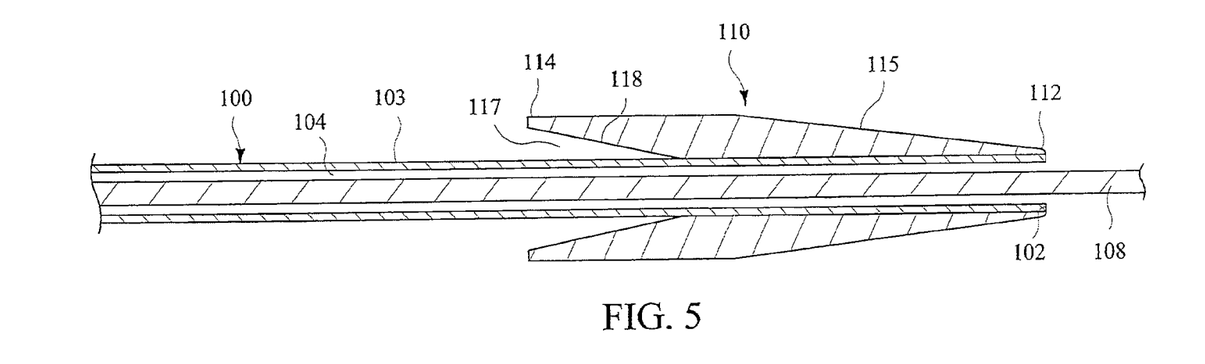
FIG. 5 is a side-sectional view of an inner cannula disposed over a wire guide.

Referring now to FIG. 5, a side-sectional view of an inner cannula 100 and an atraumatic tip 110, which may be used as part of a deployment device in conjunction with the control member 20, are shown. The inner cannula 100 comprises a tubular member having proximal and distal regions, and a lumen 104 extending between the proximal and distal regions. The lumen 104 of the inner cannula 100 is sized to allow the inner cannula 100 to be advanced over a wire guide 108, as depicted in FIG. 5.

The atraumatic tip 110 may be affixed to an exterior surface 103 along the distal region of the inner cannula 100, using a suitable adhesive or mechanical attachment mechanism, as depicted in FIG. 5. The atraumatic tip 110 may be formed from an atraumatic material, which comprises proximal and distal ends 112 and 114, respectively. The proximal end 112 comprises a smaller outer diameter relative to the distal end 114, with a taper 115 disposed therebetween. The proximal end 112 of the atraumatic tip 110 may be substantially flush with a proximal end 102 of the inner cannula 100, as depicted in FIG. 5. The atraumatic tip 110 further comprises a distal recess 117, which may be formed by providing a tapered inner surface 118 at the distal end 114 of the atraumatic tip 110, as shown in FIG. 5. As will be explained in further detail below, the distal recess 117 of the atraumatic tip 110 may receive a proximal portion of the control member 20 and the stent 60 during delivery of the stent 60 in the contracted delivery configuration.

Figure 6:
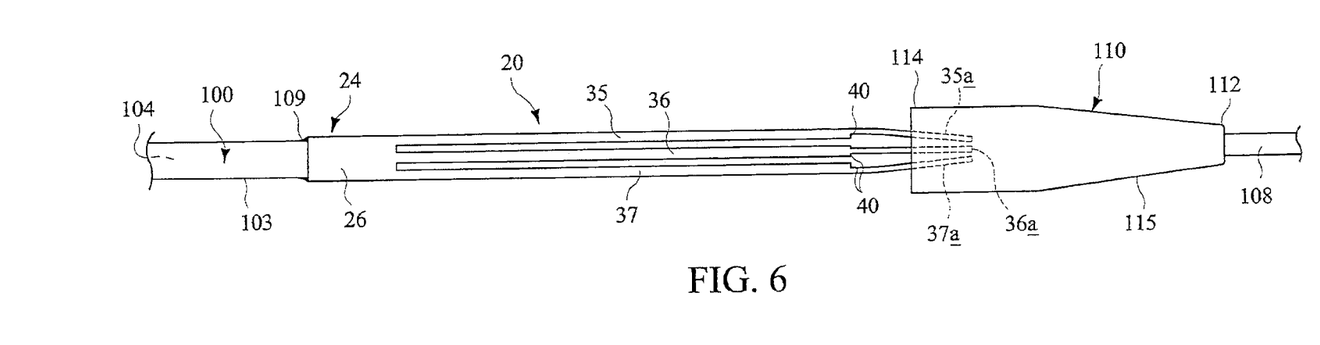
FIG. 6 is a side view of the control member of FIGS. 1-3 coupled to the inner cannula of FIG. 5.

Referring now to FIG. 6, the control member 20 of FIGS. 1-3 is coupled to the exterior surface 103 of the inner cannula 100. The distal region 24 of the control member 20 may be secured to the exterior surface 103 of the inner cannula 100 at an attachment region 109, e.g., using a solder, weld, or other suitable means. Preferably, the control member 20 is secured to the inner cannula 100 at a location such that a portion of the proximal regions 35a-37a of the tine members 35-37 may be disposed within the inner recess 117 of the atraumatic tip 110 when the tine members are in the contracted delivery configuration, as shown in FIG. 6. It should be noted that the tine members 35-39 are not rigidly secured to the inner cannula 100, but rather may expand in a radially outward direction, i.e., away from the inner cannula 100 and the atraumatic tip 110, in a deployed or partially deployed configuration.

Further, it should be noted that the inner cannula 100 extends proximally past the attachment region 109 and through the tine members 35-37. A portion of the inner cannula 100, which is disposed beneath the tine members 35-37, is not shown in FIG. 6 for illustrative purposes. However, the proximal end 102 of the inner cannula extends distal to the tine members 35-37 and may be affixed to the proximal end 112 of the atraumatic tip 110, as shown in FIG. 5.

Figure 7:
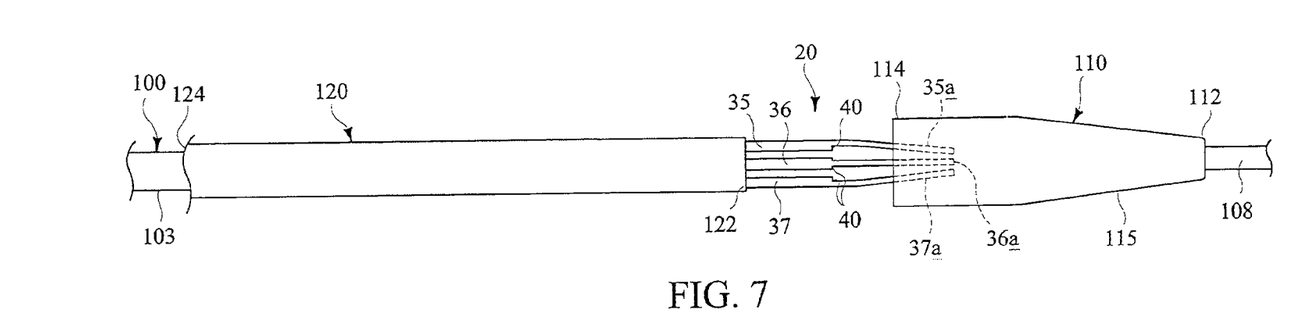
FIG. 7 is a side view showing an outer cannula disposed over a portion of the apparatus of FIG. 6

Referring now to FIG. 7, a side view illustration depicts an outer cannula 120 disposed over the apparatus of FIG. 6. The outer cannula 120 comprises proximal and distal regions and a lumen 124 extending therebetween. The lumen 124 comprises an inner diameter that is larger than an outer diameter of the inner cannula 100, thereby permitting movement of the outer cannula 120 over the inner cannula 100. As will be set forth in FIGS. 9-10 below, longitudinal movement of outer cannula 120 with respect to the inner cannula 100 permits selective expansion and retraction of the tine members 35-39 of the control member 20, thereby facilitating controlled expansion, and if necessary contraction, of the stent 60.

Figure 8:
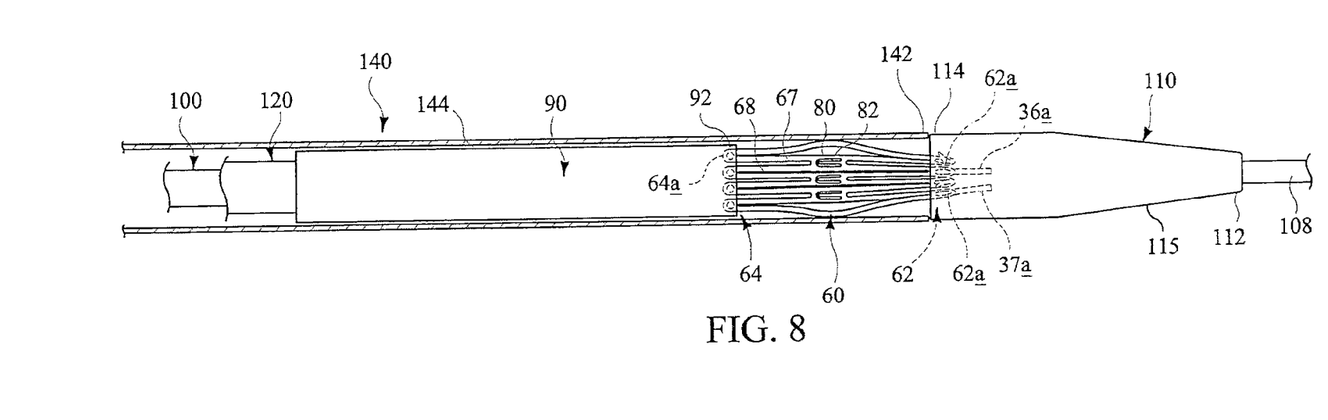
FIG. 8 is generally a side view illustrating the stent-graft of FIG. 4 used with the apparatus of FIGS. 5-7. An outer sheath is shown in a side-sectional format for illustrative purposes.

Referring to FIG. 8, the stent-graft 50 of FIG. 4 is coupled to the control member 20 in the contracted delivery configuration. In this state, the graft 90 of the stent-graft 50 may be placed over the outer cannula 120. At least a portion of the proximal end 62 of the stent 60 is coupled to the control member 20. Preferably, each of the alternating proximal apices 62a of the stent 60 are coupled to one of the tine members 35-39, as best seen in FIGS. 9-10 below. More specifically, the proximal region 35a of the tine member 35 may be looped through the bore 71 formed in one of the proximal apices 62a of the stent 60, as depicted in FIGS. 9-10. At this time, the stepped portion 40 of the tine member 35 may abut the proximal vertex 78 of the stent 60.

The remaining tine members 36-39 may be coupled to the other proximal apices 62a of the stent 60 in a similar manner. The stepped portions 40 on each of the tine members 35-39 may engage and/or abut the stent 60 and substantially inhibit distal movement of the stent 60. In this manner, the stent 60 may remain securely coupled to the control member 20. It should be noted that the tine members 35-39 are not disposed through the alternating proximal apices 62b, which comprise the barbs 77. Further, it should be noted that during delivery, when the stent 60 is coupled to the tine members 35-39 of the control member 20 as noted above, a proximal portion of the tine members 35-39 and a proximal portion of the stent 60 may extend into the inner recess 117 at the distal end 114 of the atraumatic tip 110, as depicted in FIG. 8.

Preferably, an outer sheath 140 is used to retain the stent-graft 50 in the contracted delivery configuration shown in FIG. 8. The outer sheath 140 has proximal and distal regions and a lumen 144 extending therebetween. A proximal end 142 of the outer sheath 140 extends over the stent 60 of the stent-graft 50, and may abut the distal end 114 of the atraumatic tip 110, as depicted in FIG. 8. With the entire assembly provided as shown in FIG. 8, the stent-graft 50 may be advanced towards a target site within a patient's vessel or duct over the wire guide 108.

Figure 9:
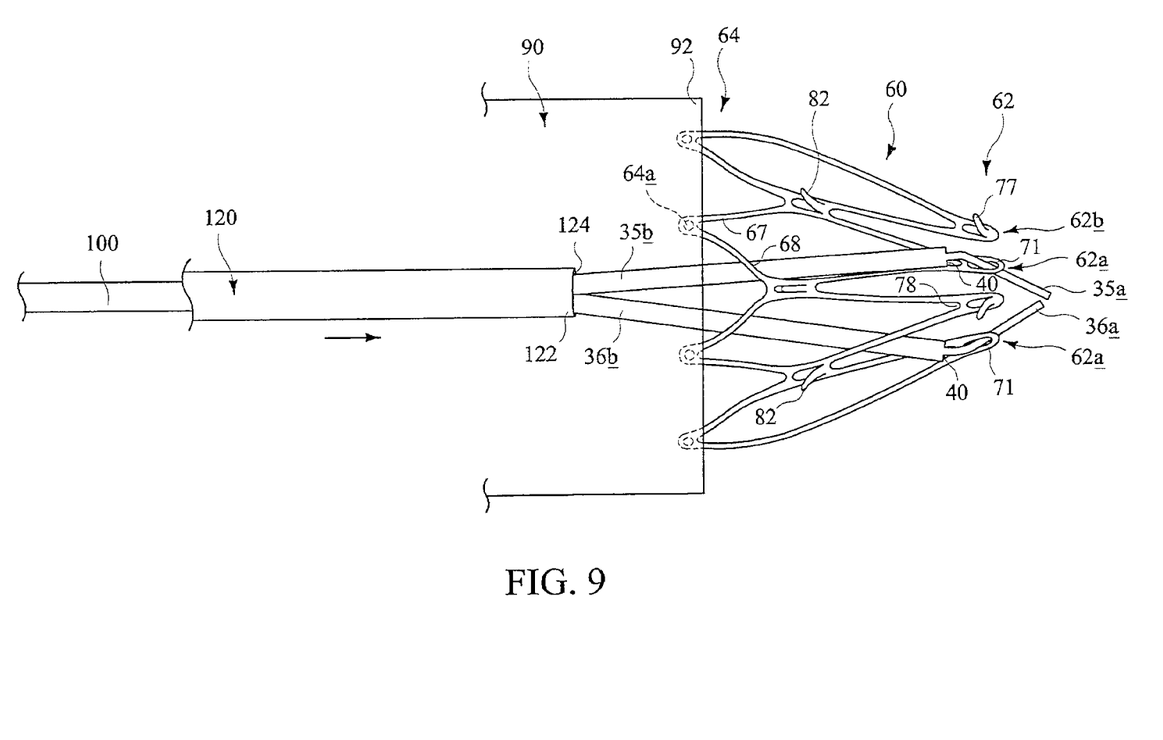
FIGS. 9-10 are side views illustrating an exemplary sequence of controlled deployment of the stent-graft of FIG. 4.
Figure 10:
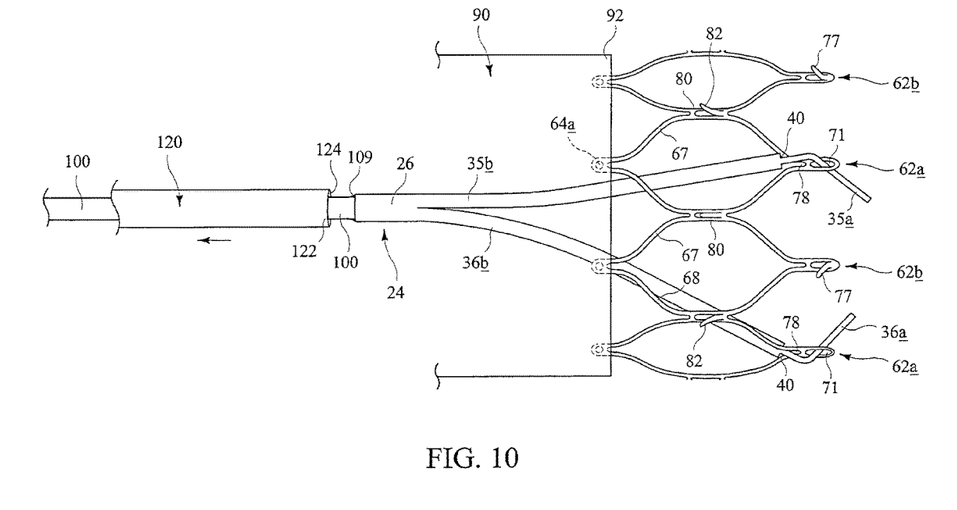

Referring now to FIGS. 9-10, prior to complete deployment of the stent-graft 50 into engagement with an inner wall of a body passage, a physician may incrementally deploy the stent 60, and also may incrementally contract the stent 60 as needed, thereby facilitating improved deployment and positioning of the stent 60. In a first step, with the apparatus delivered over the wire guide 108 as shown in FIG. 8, the stent 60 is generally aligned with a region of the body passage where it is desired to deploy the stent 60. This may be performed under fluoroscopic guidance or other suitable imaging techniques. Preferably, one or more radiopaque markers are provided on the stent 60 to facilitate alignment within the body passage.

Upon initial alignment of the stent 60, the outer sheath 140 of FIG. 8 may be distally retracted to expose the stent-graft 50. At this time, the stent 60 may partially self-expand, as depicted in FIG. 9, such that the proximal end 62 of the stent 60 may no longer engage the inner recess 117 at the distal end 114 of the atraumatic tip 110. As the proximal end 62 of the stent 60 self-expands, the stent segments begin to urge each of the tine members 35-39 in a radially outward direction, as depicted in FIG. 9.

However, the longitudinal positioning of the outer cannula 120 may be used to limit the maximum radial expansion of the tine members 35-39, which in turn may limit the maximum radial expansion of at least the proximal end 62 of the stent 60. More specifically, when the outer cannula 120 is in a relatively proximal longitudinal position, as shown in FIG. 9, the outer cannula 120 may impose a relatively stiff restraining force upon the distal regions 35b and 356b of the tine members, which may prevent the proximal regions 35a and 36a of the tine members from further radially expanding. At this time, the stent 60 cannot further radially expand. Moreover, the stent 60 cannot slide backwards, i.e., distally, because the vertices 78, angled strut segments 67 and 68, or other strut portions will engage the stepped portion 40 of the tine members 35-39 of the control member 20.

Accordingly, when the outer sheath 140 is in a relatively proximal longitudinal position, and the outer cannula 120 imposes a relatively stiff restraining force upon the tine members 35-39, neither the barbs 77 nor the barbs 82 engage the inner wall of the body passage. This allows a physician to reposition the location of the stent 60 within the body passage, if desired.

Referring to FIG. 10, in a next step, the outer cannula 120 may be distally retracted with respect to the inner cannula 100. When in a relatively distal longitudinal position, the outer cannula 120 may expose a greater portion of the tine members 35-39, and also may expose the cannula 26 and attachment region 109 between the control member 20 and the inner cannula 100. Since the tine members 35-39 are no longer substantially constrained, the tine members 35-39 may have greater flexibility, and the radial force provided by the desired self-expansion of the stent 60 may urge the tine members 35-39 further radially outward, as shown in FIG. 10.

In this manner, by moving the outer cannula 120 an incremental amount with respect to the inner cannula 100, the outer cannula 120 may permit movement of the tine members 35-39 an incremental amount between the contracted and expanded configurations, both in radially inward and outward directions, to facilitate positioning of the stent within the body passage. For example, as stent 60 radially expands in a controlled manner due to incremental distal retraction of the outer cannula 120, and the barbs 77 and 82 are about to engage the inner wall of the body passage, a physician may wish to proximally advance the outer cannula 120 with respect to the inner cannula 100 to recapture or retract the stent 60. Accordingly, any number of repositioning attempts may be made before final deployment of the stent 60.

Upon final positioning, the outer cannula 120 may be retracted distally a sufficient amount that causes the barbs 77 and 82 to fully engage the inner wall of the body passage. The inner cannula 100 then may be distally retracted to pull the proximal regions 35a and 36a of the tine members 35 and 36, as well as the other tine members, through their associated bores 71 in the stent. The tine members 35-39 then may be retracted distally into the confines of the outer cannula 120, and the inner and outer cannulas 100 and 120 may be removed from the patient's body.

Advantageously, the provision of a delivery system employing a control member 20, as described above, may permit improved positioning of the stent-graft 50 inside of a body, and also permits an amount of recapture of the stent 60 prior to full deployment. Moreover, any undesirable foreshortening, which typically occurs when conventional trigger wires release a stent, may be reduced or eliminated by use of the control member 20 and associated tine members.

Figure 11:
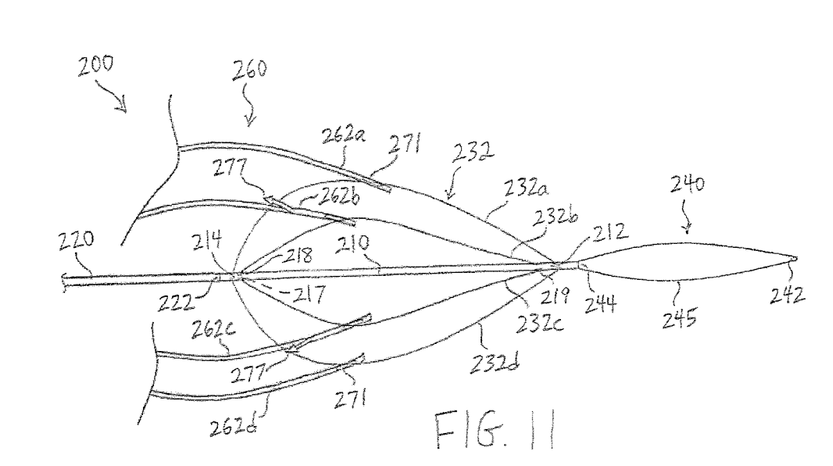
FIG. 11 is a side schematic view illustrating an alternative control member for deploying a portion of a stent-graft.
Figure 12:
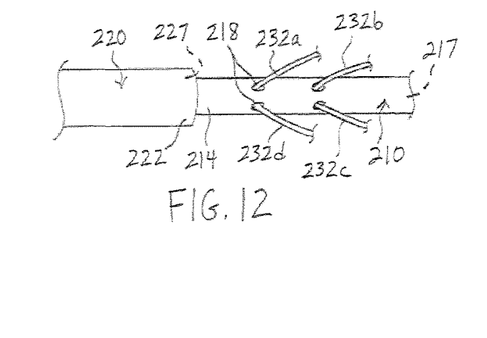
FIG. 12 is a side view illustrating an enlarged view of a portion of the control member of FIG. 11.

Referring now to FIGS. 11-12, a side schematic view illustrating an alternative system 200 for deploying a portion of a stent-graft is shown. The system 200 comprises an inner cannula 210, an outer cannula 220 and a plurality of trigger wires 232, as generally shown in FIGS. 11-12.

The inner cannula 210 comprises a proximal end 212 that terminates near an atraumatic tip 240. The atraumatic tip 240 comprises proximal and distal ends 242 and 244, and a central region 245. In one non-limiting example, the central region 245 has an outer diameter that is larger than outer diameters of the proximal and distal ends 242 and 244. Other features of the atraumatic tip 240 are similar to the atraumatic tip 110 described above.

The inner cannula 210 extends distally away from the proximal end 212, and has a distal end that terminates outside of a patient's body. The plurality of trigger wires 232 are housed at least partially within a lumen 217 of the inner cannula 210, as shown in FIGS. 11-12. In the example of FIGS. 11-12, four trigger wires 232a-232d are depicted, although it may be apparent that any suitable number of trigger wires 232 may be used to permit selective deployment of a stent as described herein.

In the embodiment of FIGS. 11-12, the trigger wires 232a-232d have distal ends that are outside of the patient's body for manipulation by a physician, and then extend in a proximal direction within the lumen 217 of the inner cannula 210. The trigger wires 232a-232d then extend radially outward through apertures 218 disposed near region 214 of the inner cannula 210, such that the trigger wires 232a-232d extend outside of the inner cannula 210, as shown in FIG. 11 and a close-up view of FIG. 12. The trigger wires 232a-232d extend proximally outside of the inner cannula 210 for a predetermined distance, and then re-enter the lumen 217 of the inner cannula 210 through apertures 219 disposed near the proximal end 212 of the inner cannula 210, as depicted in FIG. 11.

During the predetermined distance in which the trigger wires 232a-232d extend outside of the inner cannula 210, the trigger wires 232a-232d are coupled to at least a portion of a stent 260. The stent 260 may be similar to the stent 60 described in FIG. 4 above, and optionally may be part of a stent-graft assembly. In the example of FIG. 11, the stent 260 comprises a plurality of proximal apices 262a-262d, which are similar to the alternating proximal apices 62a and 62b of FIG. 4 above. In this example, the first proximal apex 262a comprises a bore 271 formed therein, and the trigger wire 232a is disposed through the bore 271. The other proximal apices 262b-262d also comprise bores 271 formed therein, and the associated trigger wires 232b-232d are each disposed through the corresponding bores 271. Select proximal apices, in this instance proximal apices 262b and 262c, may comprise barbs 277, which may be integrally formed as described with respect to the barbs 77 above, or may be external barbs secured to portions of the proximal apices.

It will be appreciated that while it is depicted that the number of trigger wires 232 corresponds directly to the number of proximal apices of the stent 260, fewer trigger wires 232 may be used. As one example, the trigger wires 232 may be coupled only to alternating proximal apices in the manner described above with respect to the tine members 35-39, in the manner shown in FIGS. 9-10 above.

The outer cannula 220 may be similar to the outer cannula 120 described above, and comprises a proximal region 222, a distal region outside of the patient's body (not shown), and a lumen 227 extending therebetween. The lumen 227 of the outer cannula 220 comprises an inner diameter that is larger than an outer diameter of the inner cannula 210, as depicted in FIG. 12, thereby permitting selective movement of the outer cannula 220 over the inner cannula 210.

In use, the stent 260 is coupled to the plurality of trigger wires 232 in a contracted delivery configuration. More specifically, portions of the trigger wires 232 are looped through the bores 271 formed in the proximal apices of the stent 260, as generally described above. While the trigger wires 232 generally hold the associated portions of the stent 260 in a contracted delivery state, the outer sheath 140 of FIG. 8 above may be used to retain the stent 260 in the contracted delivery configuration. The stent 260, or associated stent-graft, then may be advanced towards a target site within a patient's vessel or duct over a wire guide, such as the wire guide 108 if FIG. 8 above.

Incremental deployment of the stent 260 is similar to deployment of the stent 60 described above. In a first step, the apparatus is delivered over the wire guide and the stent 260 is generally aligned with a region of the body passage where it is desired to deploy the stent 260. This may be performed under fluoroscopic guidance or other suitable imaging techniques. Preferably, one or more radiopaque markers are provided on the stent 260 to facilitate alignment within the body passage.

Upon initial alignment of the stent 260, the outer sheath 140 may be distally retracted to expose the stent 260. At this time, the stent 260 may partially self-expand, as depicted in FIG. 11, such that the proximal ends 262a-262d of the stent 260 may extend partially radially outward. Some slack may be provided in the trigger wires 232a-232d between the regions 212 and 214 of the inner cannula 210, allowing for partial deployment of the proximal ends 262a-262d of the stent 260, as shown in FIG. 11.

However, the longitudinal positioning of the outer cannula 220 may be used to manipulate the portion of the trigger wires 232a-232d disposed between the regions 212 and 214 of the inner cannula 210, which in turn may affect radial expansion of at least the proximal end of the stent 260. More specifically, when the outer cannula 220 is in a relatively distal longitudinal position, as shown in FIG. 11, the outer cannula 220 does not impose a significant force, if any, upon the trigger wires 232, thereby allowing for slack in the trigger wires and partial deployment of the proximal end of the stent 260. However, the outer cannula 220 may be advanced proximally so that its proximal region 222 impinges upon at least a portion of the trigger wires, thereby reducing the slack in the trigger wires 232a-232d and causing the proximal apices 262a-262d, which are coupled to the trigger wires 232a-232d, to move in a radially inward direction. During this sequence, the barbs 277 will not engage the inner wall of the body passage. This allows a physician to reposition the location of the stent 260 within the body passage, if desired.

When proper positioning of the stent 260 is confirmed, after any number of partial deployments of the stent 260 using longitudinal manipulation of the outer cannula 220 to selectively impinge upon the trigger wires 232, then the outer cannula 220 may be moved to a distal position that is proximal to the trigger wire exit region 214. A physician may then deploy the trigger wires 232, either simultaneously or one at a time, according to known techniques, such as removing trigger wire locks and then retracting the trigger wires within the lumen of the inner cannula 210. At this time, the trigger wires 232 no longer engage the proximal apices 262a-262d of the stent 260, thereby allowing for full radial deployment of the proximal apices 262a-262d, and engagement of the barbs 277 at a desired site.

Advantageously, as with the embodiment of FIGS. 1-10 above, the system 200 of FIG. 11 provides a delivery system that may permit improved positioning of the stent 260 inside of a body. The system 200 also permits an amount of recapture of the stent 260 prior to full deployment.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A system for deploying a stent, the system comprising:
   an inner cannula having proximal and distal ends and a lumen disposed therebetween;
   first and second apertures formed in the inner cannula, where the second aperture is disposed distal to the first aperture;
   at least one trigger wire,
   wherein the at least one trigger wire extends at least partially within the lumen of the inner cannula, and further has an exposed portion extending radially outside of the lumen of the inner cannula from the second aperture, where the exposed portion of the at least one trigger wire engages an associated portion of a stent in a delivery state, and a proximal end of the at least one trigger wire extends through the first aperture into the lumen of the inner cannula when in the delivery state; and wherein the stent has a proximal end and a distal end and the second aperture is disposed between the distal end and the proximal end of the stent when the stent is in the delivery state and the first aperture is disposed proximal to the proximal end of the stent when the stent is in the delivery state,
   the at least one trigger wire having a first end that terminates proximal to the stent when in the delivery state, and
   an outer cannula sized for longitudinal movement over a portion of the inner cannula,
   the outer cannula being disposed internal to the stent in the delivery state,
   where selective distal retraction of the outer cannula distally beyond the exposed portion of the at least one trigger wire permits partial deployment of the stent to an extent of slack provided by the at least one trigger wire, and
   where selective proximal advancement of the outer cannula over the exposed portion of the at least one trigger wire incrementally urges the exposed portion of the at least one trigger wire in a radially inward direction to radially constrain the associated portion of the stent.

2. The system of claim 1 where an outer diameter of the associated portion of the stent is less than an inner diameter of a body lumen in a partial deployment state.

3. The system of claim 1 wherein the exposed portion of the at least one trigger wire is positioned between the first and second apertures.

4. The system of claim 3 wherein the second aperture is positioned adjacent to the proximal end of the inner cannula.

5. The system of claim 1 where the at least one trigger wire is sized to be advanced through a bore of the stent.

6. The system of claim 1 further comprising a plurality of trigger wires, where the plurality of trigger wires are coupled to alternating apices of the stent.

7. The system of claim 1 where the lumen of the inner cannula permits advancement of the inner cannula over a wire guide.

8. The system of claim 1 further comprising an atraumatic tip disposed on the proximal end of the inner cannula.

9. A method for deploying a stent, the method comprising:
   providing a system comprising an inner cannula having proximal and distal ends and a lumen disposed therebetween; at least one trigger wire extending at least partially within the lumen of the inner cannula, and further having an exposed portion extending radially outside of the lumen of the inner cannula, where the exposed portion of the at least one trigger wire engages an associated portion of a stent in a delivery state; and an outer cannula sized for longitudinal movement over a portion of the inner cannula;
   selectively distally retracting the outer cannula distally beyond the exposed portion of the at least one trigger wire to permit partial deployment of a proximal end of the stent to an extent of slack provided by the at least one trigger wire, selectively proximally advancing the outer cannula over the exposed portion of the at least one trigger wire prior to full radial deployment of the stent to directly engage and incrementally urge the exposed portion of the at least one trigger wire in a radially inward direction to radially constrain the associated portion of the stent; and when proper positioning of the stent is confirmed, distally retracting the outer cannula.

10. The method of claim 9 where an outer diameter of the associated portion of the stent is less than an inner diameter of a body lumen in a partial deployment state.

11. The method of claim 9 further comprising providing at least first and second apertures formed in the inner cannula, where the second aperture is disposed distal to the first aperture, and where the exposed portion of the at least one trigger wire is positioned between the first and second apertures.

12. The method of claim 11 where the second aperture is positioned adjacent to the proximal end of the inner cannula.

13. The method of claim 9 where the at least one trigger wire is sized to be advanced through a bore of the stent.

14. The method of claim 9 further comprising providing a plurality of trigger wires, where the plurality of trigger wires are coupled to alternating apices of the stent.

15. The method of claim 9 further comprising advancing the inner cannula over a wire guide.

16. The method of claim 9 further comprising providing an atraumatic tip disposed on the proximal end of the inner cannula.

17. A system for deploying a stent, the system comprising:
an inner cannula having proximal and distal ends and a lumen disposed therebetween, and further having at least a first and a second aperture formed therein;
at least one trigger wire,
wherein the at least one trigger wire extends at least partially within the lumen of the inner cannula from the second aperture, and further has an exposed portion extending radially outside of the lumen of the inner cannula, where the exposed portion of the at least one trigger wire engages an associated portion of a stent in a delivery state, where the second aperture is disposed distal to the first aperture, and where the exposed portion of the at least one trigger wire is positioned between the first and second apertures and a proximal end of the at least one trigger wire extends through the first aperture into the lumen of the inner cannula when in the delivery state and wherein the stent has a proximal end and a distal end and the second aperture is disposed between the distal end and the proximal end of the stent when the stent is in the delivery state and the first aperture is disposed proximal to the proximal end of the stent when the stent is in the delivery state, the at least one trigger wire having a first end that terminates proximal to the stent when in the delivery state; and an outer cannula sized for longitudinal movement over a portion of the inner cannula, the outer cannula being disposed internal to the stent in the delivery state, where selective distal retraction of the outer cannula distally beyond the exposed portion of the at least one trigger wire permits partial deployment of the stent to an extent of slack provided by the at least one trigger wire, where an outer diameter of the associated portion of the stent is less than an inner diameter of a body lumen in a partially deployed state, and where selective proximal advancement of the outer cannula over the exposed portion of the at least one trigger wire incrementally urges the exposed portion of the at least one trigger wire in a radially inward direction to radially constrain the associated portion of the stent.

18. The system of claim 17 where the at least one trigger wire is sized to be advanced through a bore of the stent.

19. The system of claim 17 further comprising a plurality of trigger wires, where the plurality of trigger wires are coupled to alternating apices of the stent.

20. The system of claim 17 where the lumen of the inner cannula is configured to permit advancement of the inner cannula over a wire guide.

\* \* \* \* \*